United States Patent
Ahmed (10) Patent No.: US 7,780,092 B2
(45) Date of Patent: Aug. 24, 2010

(54) APPLICATION OF MICROSYSTEMS FOR REAL TIME IEQ CONTROL

(75) Inventor: Osman Ahmed, Hawthorn Woods, IL (US)

(73) Assignee: Siemens Industry Inc., Alpharetta, GA (US)

(*) Notice: Subject to any disclaimer, the term of this patent is extended or adjusted under 35 U.S.C. 154(b) by 776 days.

(21) Appl. No.: 11/513,337

(22) Filed: Aug. 30, 2006

(65) Prior Publication Data

US 2007/0067063 A1 Mar. 22, 2007

Related U.S. Application Data (60) Provisional application No. 60/712,870, filed on Aug. 30, 2005.

(51) Int. Cl.
  *G05D 23/24* (2006.01)
  *B60H 1/00* (2006.01)
  *B60H 1/32* (2006.01)

(52) U.S. Cl. .............. 236/91 C; 236/1 B; 236/51; 236/94; 165/212; 700/277; 73/31.02

(58) Field of Classification Search .............. 165/212; 236/1 B, 44 C, 51, 91 C, 94; 700/277; 73/31.02
See application file for complete search history.

(56) References Cited

U.S. PATENT DOCUMENTS

| | | | |
|---|---|---|---|
| 5,562,537 A | 10/1996 | Zver et al. | |
| 5,707,005 A * | 1/1998 | Kettler et al. | 236/49.3 |
| 5,751,916 A * | 5/1998 | Kon et al. | 706/2 |
| 6,137,403 A | 10/2000 | Desrochers et al. | |
| 6,199,575 B1 | 3/2001 | Widner | |
| 6,625,500 B1 | 9/2003 | Li | |
| 2001/0025349 A1 | 9/2001 | Sharood et al. | |
| 2001/0040509 A1 | 11/2001 | Dungan | |
| 2003/0058114 A1 * | 3/2003 | Miller et al. | 340/577 |
| 2004/0008651 A1 * | 1/2004 | Ahmed | 370/338 |
| 2004/0019392 A1 | 1/2004 | Hirai | |
| 2004/0088082 A1 | 5/2004 | Ahmed | |
| 2004/0144849 A1 * | 7/2004 | Ahmed | 236/1 E |
| 2004/0249479 A1 | 12/2004 | Shorrock | 700/28 |
| 2004/0263351 A1 | 12/2004 | Joy et al. | 340/870.01 |

(Continued)

FOREIGN PATENT DOCUMENTS

EP 0 068 289 1/1983

(Continued)

OTHER PUBLICATIONS

PCT Search Report—PCT/US2006/033565—mailed Jan. 19, 2007.

*Primary Examiner*—Frantz F. Jules
*Assistant Examiner*—Daniel C Comings
(74) *Attorney, Agent, or Firm*—Thomas J. Burton (57) ABSTRACT

An arrangement includes a plurality of wireless microsystems and a central data processor. Each microsystem is operable to measure a plurality of indoor environmental quality-related parameters and is operable to communicate first information pertaining to the measured parameters wirelessly to a network device. The central data processor is operably coupled to receive the first information from the network device, and further configured to generate a metric value of an indoor environmental quality of at least a first space based at least in part on the first information, the metric value dependent upon each of the measured parameters of at least a first of the plurality of microsystems.

22 Claims, 5 Drawing Sheets

U.S. PATENT DOCUMENTS

2005/0270151 A1* 12/2005 Winick .................... 340/539.1

FOREIGN PATENT DOCUMENTS

| | | |
|---|---|---|
| EP | 1 696 371 | 8/2006 |
| WO | WO 99/57697 | 11/1999 |
| WO | WO 00/54237 | 9/2000 |
| WO | WO 01/26330 | 4/2001 |
| WO | WO 01/35190 | 5/2001 |
| WO | WO 01/93220 | 12/2001 |
| WO | WO 2004/038525 | 5/2004 |

* cited by examiner

APPLICATION OF MICROSYSTEMS FOR REAL TIME IEQ CONTROL

This application claims the benefit of U.S. Provisional patent application Ser. No. 60/712,870, filed Aug. 30, 2006, which is incorporated herein by reference.

FIELD OF THE INVENTION

The present invention relates to indoor environmental control.

BACKGROUND

Buildings in which people work and live have systems that monitor and sustain the comfort level of the building environment. Such systems include heating, ventilation and air conditioning (HVAC) systems, lighting systems, as well as others. HVAC and lighting systems have existed, at least at some level, for thousands of years.

HVAC and lighting systems have become sophisticated, and are often able to maintain careful balances of humidity and temperature, as well as provide fresh air and adequate light within buildings. Suitable temperature, humidity, light and oxygen levels contribute to the indoor environmental quality of a building or work place. Good environmental quality can translate to better productivity and health of the occupants.

While the importance of environmental quality has been realized, to date there has been no reliable or comprehensive way to quantify or measure the indoor environmental quality of a building. Temperatures can be maintained, and light fixtures kept operational, but these alone cannot provide any granular measurement of indoor environmental quality (IEQ).

Thus, although the building industry has experienced a tremendous interest in the subject due to proven research that links IEQ to health and productivity, the scope of IEQ measurement remains within the bounds of spot-checking of conditions, intermediate sampling of conditions using portable data logging computers, and some limited monitoring of some parameters. These solutions are either not cost effective, or at least would not be if implemented to the extent necessary to generate comprehensive monitoring.

There is a need, therefore, for a more comprehensive system for monitoring and/or measuring parameters from which IEQ may be determined.

SUMMARY OF THE INVENTION

The present invention addresses the above described needs, as well as others, by employing wireless MEMS microsystem which are configured to measure a plurality of parameters relating to IEQ, and communicate these parameters, preferably wirelessly, to data processing equipment. The use of MEMS in sufficient quantities for this purpose makes possible real-time IEQ monitoring and/or control.

A first embodiment of the invention includes a plurality of wireless microsystems and a data processor. The Microsystems are operable to measure a plurality of indoor environmental quality-related parameters and operable to communicate first information pertaining to the measured parameters wirelessly to a network device. The data processor is operably coupled to receive the first information from the network device, and is further configured to generate a metric value of an indoor environmental quality of at least a first space based at least in part on the first information, the metric value dependent upon each of the measured parameters of at least a first of the plurality of microsystems.

In other embodiments, some or all of the microsystems need not be wireless. However, there is an advantage to the use of wireless microsystems because it reduces labor and material costs associated with running wires.

In some embodiments, the data processor and the network device form a part of a field controller device. In other configurations, the data processor is in the form of a more centralized control station of a facility. In still other embodiments, the network device is a wireless or wired communication hub with or without controller capability.

The above described features and advantages, as well as others, will become more readily apparent to those of ordinary skill in the art by reference to the following detailed description and accompanying drawings.

DETAILED DESCRIPTION

Figure 1:
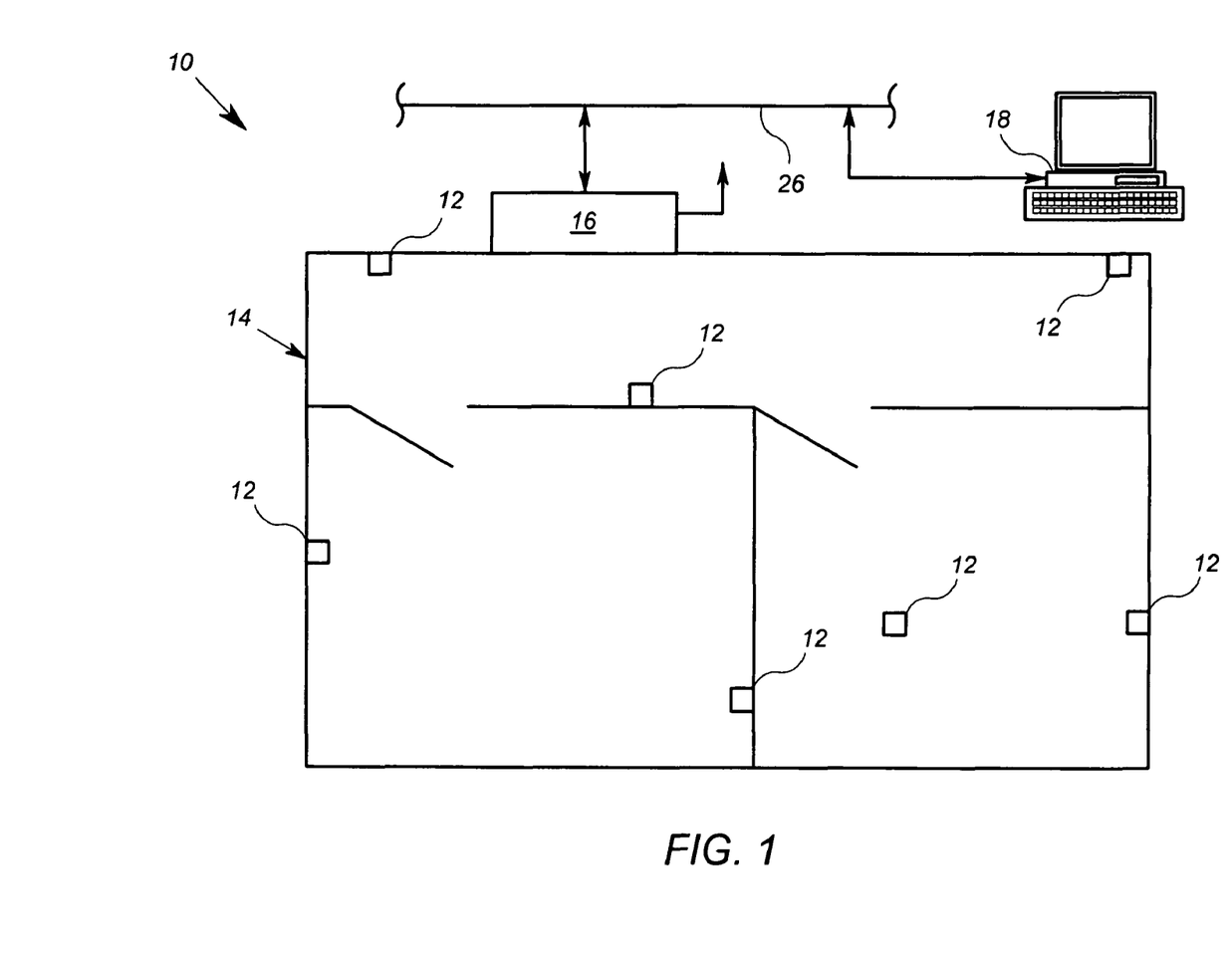
FIG. 1 shows a schematic block diagram of an exemplary embodiment of an arrangement according to the invention.

FIG. 1 shows an arrangement 10 that includes a plurality of wireless microsystems 12, each microsystem 12 is operable to measure a plurality of IEQ related parameters in a building environment 14 and is further operable to communicate the parameters wirelessly to a network device 16. The network device 16 is operable to communicate the parameters of the plurality of microsystems 12 to a central data processor 18 that is able to generate a metric of the IEQ based on the parameters, and to update the metric in an ongoing basis.

Figure 2:
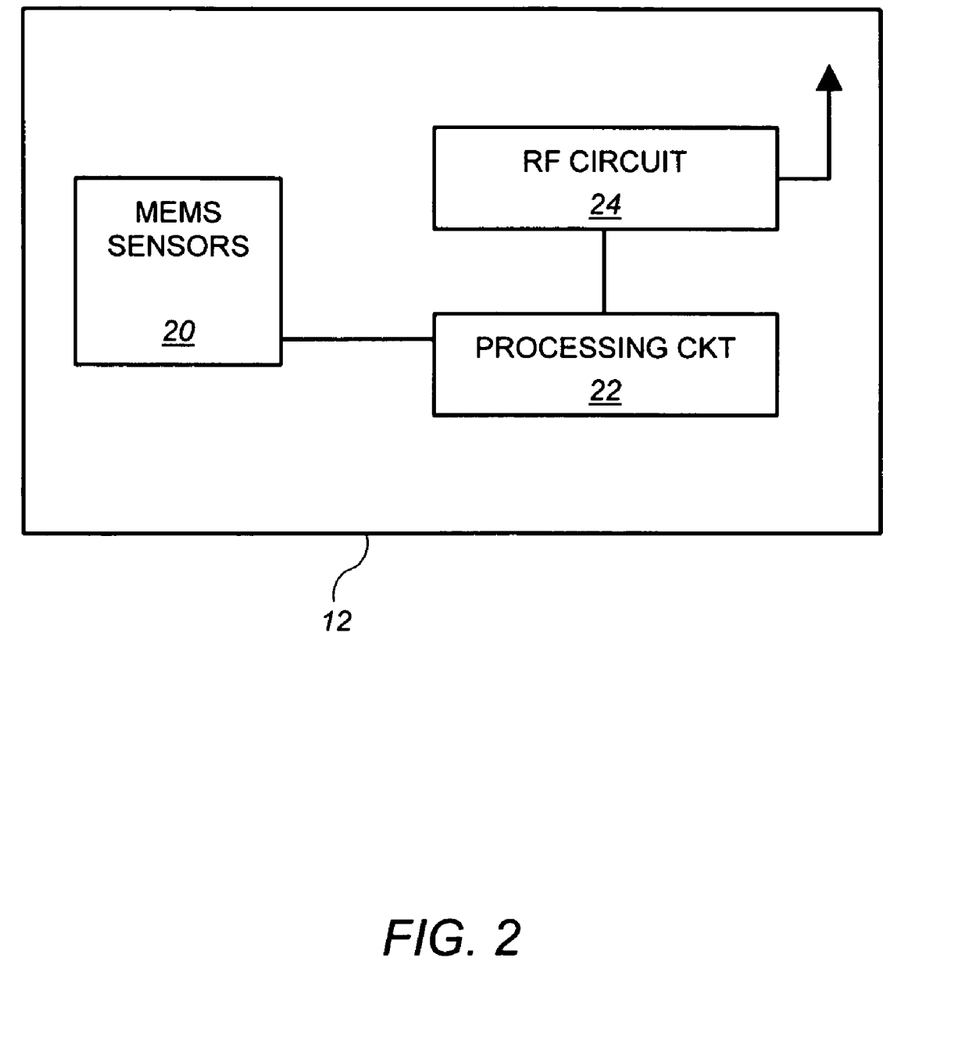
FIG. 2 shows a block diagram of an exemplary microsystem device that may be used in the arrangement of FIG. 1.

Referring to FIG. 2, the current state of the art of microsystems is sufficient to create a microsystem operable to measure and/or monitor IEQ parameters such as total volatile organic compounds (TVOC), temperature, mean radiant temperature, air flow rate, CO, $CO_2$, relative humidity, light level, and even sound. Each microsystem 12 may therefore employ MEMS sensors 20 that measure some or all of these values. The microsystem 12 may also incorporate processing circuitry 22, as well as radio frequency transmission circuitry 24. General examples of MEMS devices having processing circuitry and RF capability are discussed in U.S. patent application Ser. No. 10/353,142 entitled "Building System with Reduced Wiring Requirements and Apparatus for Use Therein", filed Jan. 28, 2003, and U.S. patent application Ser. No. 10/672,527, filed Sep. 26, 2003, entitled "Building Control System Using Integrated MEMS Device", both of which are incorporated herein by reference. Other devices of this nature are known.

In one embodiment, the processing circuitry 22 is programmed or otherwise configured to generate an IEQ index based on the various information obtained by the MEMS sensors 20, and cause the RF circuit 24 to communicate that index wirelessly to the network device 16. In other embodiments, the processing circuitry 22 merely obtains the sensor values and provides those values (preferably with some low pass filtering) to the RF circuit 24 for transmission to the network device 16. The RF circuit 24 may suitably use Bluetooth or other short range RF transmission technology. The microsystem 12 may further include a battery, not shown, to power the operations.

Referring again to FIG. 1, the network device 16 may suitably be an RF transceiver connected to a building control system wired or wireless network 26, such the wireless network described in U.S. patent application Ser. No. 10/353, 142, the disclosure of which is incorporated herein by reference.

The central data processor 18 may suitably be a computer workstation that is connected to the building control system network 26. In other embodiments, the IEQ arrangement 10 may use its own network, or another network. In the embodiment in which the IEQ arrangement 10 uses a building control system network, then the central data processor 18 may suitably be a control station of the building control or automation system, such as an INSIGHT™ Workstation available from Siemens Building Technologies, Inc. of Buffalo Grove Illinois, and which is used in the APOGEE™ brand automation systems.

The central data processor 18 may utilize the IEQ data to control various HVAC, lighting or other parameters to improve the IEQ. Otherwise, the central data processor 18 may make the information available to a technician through visible display or further communication via Internet, e-mail or otherwise.

One advantage of some embodiments of the invention is that the microsystems 12 may be employed extensively throughout the building, thereby providing comprehensive IEQ data from throughout the building 14. The central data processor 18 may be able to identify local areas of poor quality, as well as the overall comfort level of the building 14. The microsystems 12 may be placed on walls, fixtures, the floor, and even on moveable objects such as furniture or modular walls.

Figure 3:
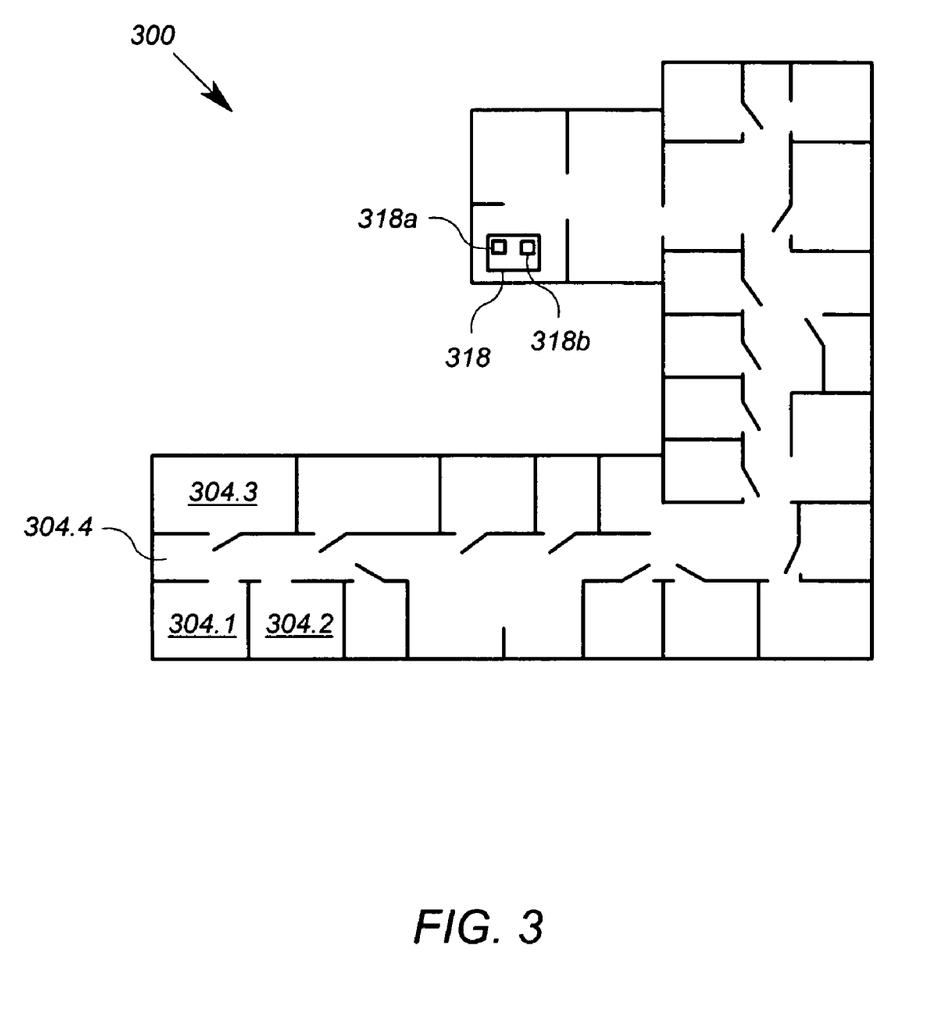
FIG. 3 shows a top floorplan view of a floor of a building that may employ an arrangement according to an embodiment of the invention.
Figure 4:
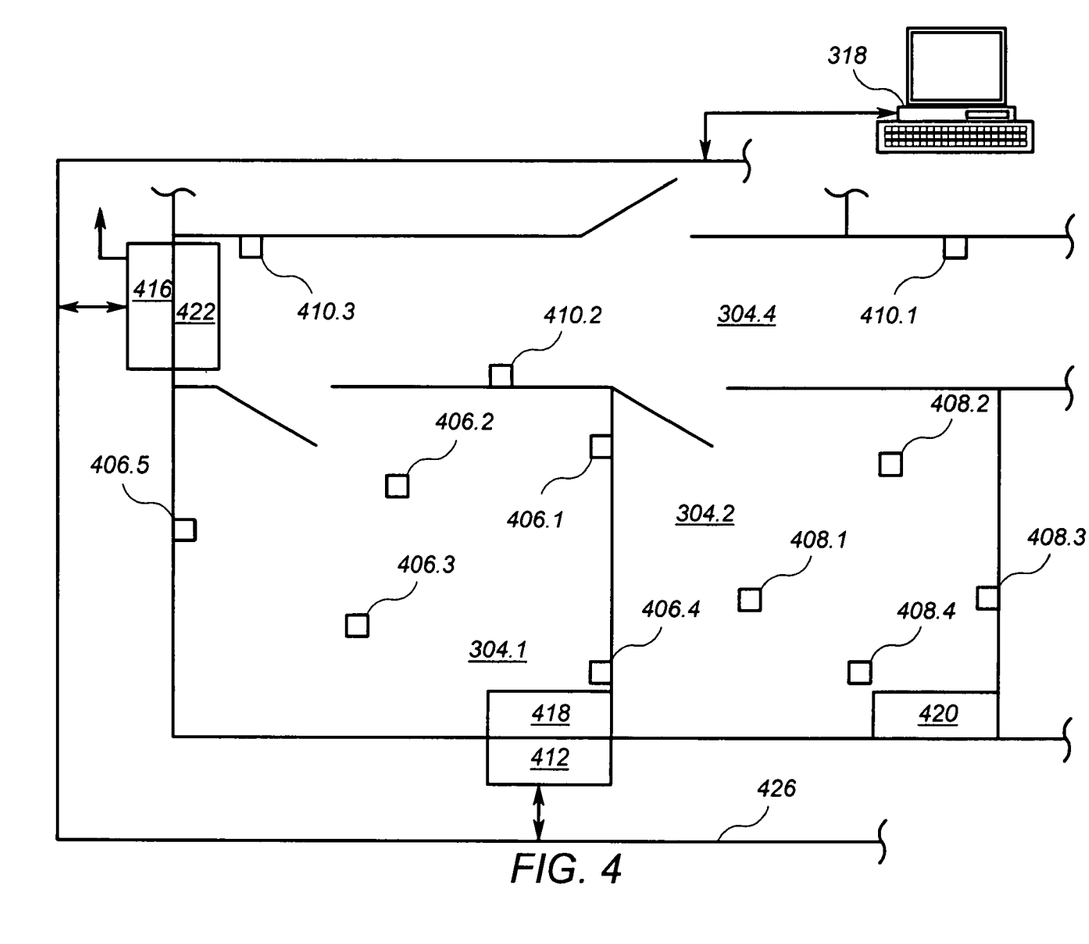
FIG. 4 shows a schematic view of a portion of the building of FIG. 3 with an exemplary arrangement according to an embodiment disposed therein.

FIGS. 3 and 4 show in detail another embodiment of an arrangement for use in a building to control and/or monitor IEQ. FIG. 3 shows a top floor plan view of building 300 that includes a plurality of spaces, illustrated by way of example as rooms 304.1, 304.2, 304.3 and hallway 304.4. Each of the spaces of the building 300 has a set of building control devices, not shown in FIG. 3, that are used to monitor and affect environmental conditions in a space. The building also includes at least one control station 318, that is operably coupled to exchange data regarding environmental conditions in the various spaces 304.1, 304.2, etc.

The control station 318 may suitably be a general purpose computer, including a data processing device 318a and user interface devices 318b as is known in the art, which is configured to carry out the operations described herein. The control station 318 may suitably be an INSIGHT® Workstation or other building systems control station computer, programmed and/or otherwise modified to carry out the operations ascribed to the control station 318 as described herein.

FIG. 4 shows in further detail a combination floor plan/block diagram schematic of the portions the building 300 of FIG. 3. FIG. 4 shows rooms 304.1, 304.2, a portion of the hallway 304.4, and the central control station 318. As discussed above, each room or space has a set of devices that cooperate to allow monitoring of and/or control of environmental conditions in the room or space. Each room of the building 300 may be configured similarly to rooms 304.1 and 304.2 as shown in FIG. 4.

Referring specifically to FIG. 4, the room 304.1 includes a plurality of microsystems 406.1-406.5, and a variable air volume ("VAV") unit 418. The microsystems 406.1-406.5 are wireless sensor and communication devices that have the capability to measure a plurality of IEQ-related values, preferably including one or more non-traditional HVAC values such as total volatile organic compounds, $CO_2$, CO, light or sound. In the embodiment described herein, the Microsystems 406.1-406.5 can measure temperature, humidity, TVOCs, $CO_2$, CO, light and air flow. As discussed above, technology for combining multiple MEMs type sensors is known in the art. The general configuration of the microsystems 406.x may be similar to that of the microsystem 12 of FIG. 2, discussed further above.

The VAV unit 418 is a device known in the art that is used to control the flow of air into the space 304.1 from a ventilation shaft, not shown. The air flowing from the ventilation shaft may be heated or chilled, and is provided from source at a remote location within the building, as is known in the art. As a consequence, the VAV unit 418 may alter the temperature of the room 304.1 by increasing or decreasing the flow of air. The VAV unit 418 may also include heating or cooling coils that are capable of locally altering the temperature of the air flowing into the room 304.1. As is also known in the art, the VAV unit 418 further includes an actuator, not shown separately, that is operable to translate control signals to movement of a mechanical damper that increases or decreases the flow of air into the room 304.1.

Each of the microsystems 406.1-406.5 is operable to communicate wirelessly to a network device in the form of a proximally located field controller 412. The field controller 412 may take the general form of a control device in a commercially available building automation system field panel, which has been modified to include short range wireless communication capabilities for communication with the Microsystems. However, in some embodiments, the field controller 412 may simply comprise another wireless microsystem device, such as is the case in the system disclosed in U.S. patent application Ser. Nos. 10/353142 and 10/672527, both of which are incorporated herein by reference.

The field controller 412 is also operably coupled to control the operation of the VAV unit 418. In general, the field controller 412 is operable to generate control signals for the VAV unit 418 to control the temperature and/or other environmental conditions within the space 314. In accordance with aspects of the present invention, the field controller 418 is also operable to generate a metric regarding the indoor environmental quality (IEQ) of the room 304.1. The field controller 418 is also operably configured to communicate with the control station 318 via a network 426.

similar to the room 304.1, the room 304.2 includes a plurality of microsystems 408.1-408.4, and a VAV unit 420. The Microsystems 408.1-408.4 are wireless sensor and communication devices that are preferably identical to the microsystems 406.1-406.5, and thus have the capability to measure a similar set of IEQ-related values. The VAV unit 420 is preferably similar to the VAV unit 418 in design and capability. Each of the microsystems 408.1-408.4 is operable to communicate wirelessly to the proximally located field controller 412. The field controller 412 is also operably coupled to control the operation of the VAV unit 420. As with the VAV unit 418, the field controller 412 is operable to generate control signals for the VAV unit 420 to control the temperature and/or other environmental conditions within the space 304.2. In accordance with aspects of the present invention, the field controller 412 is also operable to generate a metric regarding the indoor environmental quality (IEQ) of the room 304.2.

Thus, the field controller 412 is shared in this embodiment by the rooms 304.1 and 304.2. In general, the field controller 412 will typically generate control signals VAV units (or other devices) in one or more rooms, but less than all of the rooms in the building 300.

In the embodiment described herein, each field controller such as the field controller 412 may suitably be associated with one or two rooms, or about 1000 square feet of large open area, in order to limit the distance over which wireless communication with each rooms' Microsystems must take place. In other words, if the field controller 412 were associated with a large number of rooms, then the field controller 412 may be relatively distant from some of the rooms. In such a case, the Microsystems of the distant rooms may require more power to carry out the necessary communications. The requirement of higher transmission power for is undesirable because it taxes the limited energy resources on the microsystem. However, it is possible that each room could have a single hub microsystem unit that has wired power which could act as a relay between the wireless microsystems of each room and the field controller 412. It is also possible that the various wireless Microsystems could form a network of wireless links between any individual wireless microsystem and the field controller 412. In these alternative cases, a field controller may be used to control many more than two rooms.

The hall space 304.4 may also include a set of devices similar to those found in the rooms 304.1 and 304.2. For example, the portion of the hall space 304.4 shown in FIG. 4 includes a plurality of microsystems 410.1-410.3, and a VAV unit 422. The microsystems 410.1-410.3 are wireless sensor and communication devices that are preferably identical to the Microsystems 406.1-406.5, and thus have the capability to measure a similar set of IEQ-related values. The VAV unit 422 may suitably be similar to the VAV unit 418 in design and capability, although it may constitute a model more suitable for hallways, as would be known to those of ordinary skill in the art. Each of the microsystems 410.1-410.3 is operable to communicate wirelessly to a different field controller 416.

The field controller 416 may suitably have a similar design as the field controller 412, and is operably coupled to control the operation of the VAV unit 422. The field controller 416 is operable to generate control signals for the VAV unit 422 to control the temperature and/or other environmental conditions within the portion of hall space 304.4 shown in FIG. 4. In accordance with aspects of the present invention, the field controller 416 is also operable to generate a metric regarding the indoor environmental quality (IEQ) of the hall space 304.4.

Thus, the field controller 416 is separate from the field controller 412 that controls/monitors the environment of the rooms 304.1 and 304.2.

Both field controller 412 and 416 are operably connected to the network 426 to communicate with each other, as well as with the control station 318. As discussed above, the control station 318 may suitably be a general purpose computer configured to carry out the operations described herein. In general, the control station 318 provides a centralized location at which a human technician or operator may monitor and/or control conditions in the spaces 304.1, 304.2 and 304.4 (as well as other spaces) via the field controllers 412, 416.

In operation, the various devices in FIG. 4 operate to control the environmental conditions of the areas 304.1, 304.2 and 304.4. To this end, the field controllers 412 and 416 control the operation of the VAV units 418, 420 and 422 to control at least some conditions in the rooms 304.1, 304.2 and 304.4. In addition, the field controllers 412 may also be configured to activate light switches or other environment related devices.

Referring to the room 304.1, the field controller 412 includes the logic that performs control operations to control the flow of heated or chilled air into the room 304.1 in an attempt to maintain the temperature at a desired level. The desired temperature level is a set point value that may be set by an operator via the central control station 318, input at the field controller 412, set by a thermostat device, not shown, within the room 304.1, or otherwise provided to the field controller 412. The field controller 412 compares temperature information received from the various microsystems 406.1-406.5 to the set point value. If the temperature information indicates that the room temperature is too low relative to the set point, then the field controller 412 provides output signals that cause the VAV unit 418 to reduce the flow of chilled air into the room 304.1, or cause the VAV unit 418 to increase the flow of heated air into the room 304.1, depending upon whether the available air flow is of chilled air or heated air.

To accomplish such temperature control, the field controller 412 may suitably use any of a plurality of known control algorithms (PI, PID) to control the VAV unit 418 based on the measured temperature and the set point temperature. Because there are multiple data points regarding the temperature in the room, one for each microsystem 406.1-406.5, the field controller 412 may suitably take the mean or median measured temperature value as the value used for PI or PID control of the VAV unit 418. As is known in the art, the field controller 412 receives the temperature information from the microsystems 406.1-406.5 on a periodic basis, and periodically updates the control calculations based thereon.

In addition, the field controller 412 also obtains from each microsystem 406.1-406.5 an IEQ index value. The IEQ index value is a composite index of various sensed conditions measured by each of the microsystems 406.1-406.5. For example, the IEQ index value might be formed from a combination of values, each value expressing a correlation (or variance) between a measured value and an ideal value for human comfort. As discussed above, the microsystems 406.1-406.5 measure TVOC, $CO_2$, CO, light, temperature, humidity and air flow. The IEQ index may suitably be F ($VAR_{temp}$, $VAR_{hum}$, $VAR_{tvoc}$, $VAR_{co2}$, $VAR_{co}$, $VAR_{light}$, $VAR_{flow}$) where the $VAR_x$ values are variances of the value x from an ideal value or range.

By way of example, the value of $VAR_{temp}$ may be a normalized measure of the variance of the temperature from the range of 68° F. to 74° F., the value of $VAR_{hum}$ may be a normalize variance of the variance of the humidity from the range of 40% to 70%. The value of $VAR_{tvoc}$ may suitably be a normalized value representative of the measured total volatile organic compounds that is greater than zero. Similarly, the values $VAR_{co2}$ and $VAR_{co}$, can be a normalized value representative of the measured amount of $CO_2$ and CO, respectively. The value of $VAR_{light}$ and $VAR_{flow}$, may suitably be the variance of the measured light and flow values, respectively from their ideal values. Because the lights in a room may be off when the room is not occupied, the $VAR_{light}$ value may be set to zero if there is evidence that the room is unoccupied. To this end, one or more microsystems may have a motion sensor or other occupancy-like sensor.

It will be appreciate that there are many ways to determine IEQ, including those based on the Indoor Air Quality standards and definitions listed in ASHRAE Standards 55 and 62, which are incorporated herein by reference. The ASHRAE standards also provide information as to what constitutes "ideal" or at least healthy levels of the various IEQ parameters. It may be advantageous to measure other contaminants, such as particulates, biological compounds, inorganic compounds, etc. It will also be appreciated that the weight given to any particular variance from ideal conditions may depend on the needs and goals of building in which the system is implemented.

In any event, with proper normalization, the composite IEQ value provided by each microsystem represents how much the aggregate temperature, humidity, light, flow, TVOCs, $CO_2$ and CO conditions vary from ideal conditions for human beings. If the composite IEQ value from the Microsystems is relatively low, then the environmental conditions in the room 304.1 are considered to be of a high standard because conditions are near ideal. If the IEQ index is relatively high, then the environmental conditions in the room 304.1 are considered to be substandard. It will be appreciated that an inverse scale may be used such that a high IEQ index indicates a good environment and a low IEQ index indicates a poor environment.

The IEQ index is useful because it can detect issues with environmental quality even if no single monitored condition is particularly poor. For example, while temperature variations, low air flow, humidity variations and other conditions may generally be controlled through the normal HVAC operations, it is possible that low-normal conditions of all of these parameters in the aggregate may create a relatively poor environmental quality, although no single factor is particularly poor. Thus, it is possible that the HVAC system and lighting system are operating within normal limits for two different rooms, but the aggregate IEQs for the two rooms are very different.

One aspect of the IEQ-measurement capabilities of at least some embodiments described herein relates to the placement of multiple sensor devices in each room, such as the room 304.1. The use of multiple microsystem sensor devices 406.1-406.5 in the room 304.1 allows for a more granular measurement of IEQ within the facility. It is possible that a room generally has a good environment, but that portions of the room or space do not. The granular aspect of this embodiment, by providing multiple measurement devices in each room, obtains information for each portion of the room. The use of multiple microsystem devices in each space or room also overcomes the problem of single-point measurement where the single sensor for a room is placed in a "hot spot" or "cool spot" that is not really representative of the room conditions. Such "hot spots" or "cool spots" may relate to temperature, flow, humidity, light, volatile compound content, CO or CO2. By using multiple Microsystems in each room, the chance of an anomalous measurement greatly affecting assessment of building conditions is substantially reduced. This granularity also allows for problems to be detected more quickly, and pin-pointed more readily.

An issue that relate the use of multiple microsystems in each room arises from the fact that light measurements can be affected by things that do not relate to environmental quality. For example, if the microsystem 406.1 were located on a wall that was subsequently covered by a bookcase, then it may detect little or no light despite the fact that the space 304.1 may in general have a sufficient amount of light. One precaution that may be made to avoid artificially low light measurements is to include a motion sensor in the microsystems 406.x, 408.x and 410.x. The motion sensor of the Microsystems 406.x, 408.x and 410.x may be used to determine whether a particular microsystem such as microsystem 406.1 is covered or obscured. For example, if the motion sensor of the microsystem 406.1 detects little or no motion over a predetermined period of time (days or months) while other microsystems 406.2-406.5 in the same room 304.1 detect significant amounts of motion, then there is an indication that the particular microsystem 406.1 is covered or obscured. In such a case, the light measurement of the microsystem 406.1 that detects little or no motion may be discarded or at least given little weight.

In alternative embodiments (or in addition), the Microsystems 406.x, 408.x and 410.x may be placed on ceilings to avoid being covered. Moreover, if a large number of Microsystems are employed throughout a room, then the anomalous light measurements from covered up sensors may be statistically filtered out by averaging or using median values.

In any event, as discussed above, the field controller 412 calculates an IEQ value from each controller 406.1-406.5 and 408.1-408.4, or alternatively or additionally for the rooms 304.1 and 304.2, based on the information from the sensor microsystems in the rooms 304.1 and 304.2. The field controller 412 communicates the IEQ value(s) for each of the rooms 304.1 and 304.2 to the control station 318.

In the embodiment discussed herein, the field controller 412 is also configured to generate an alarm message or signal in response to an out-of-boundaries value for any of the measured values (temperature, humidity, CO2, CO, TVOC, etc.). By way of example the field controller 412 may provide any such alarm messages to the control station 318 or to another network node (i.e. another field controller such as controller 416). The handling and use of alarm messages in a building control system is well known in the art. In addition, the field controller 412 is configured to generate an alarm message based on IEQ values for a microsystem or set of Microsystems, even if no individual parameter (e.g. temperature, humidity CO2, CO, flow, TVOC, etc.) is out of normal bounds. For example, it may be that all of the parameters is in the low-normal range, such that no single value is out of range. However, with all conditions in the low normal range, the overall quality of the environment is relatively low, thereby triggering an alarm. The field controller 412 is of course also configured to generate an alarm message based on IEQ values if one or more the individual environmental parameters is out of range.

In general, as with the IEQ values themselves, the field controller 412 provides any IEQ alarm information/message to the control station 318. The control station 318 may suitably handle an IEQ value-based alarm message in a manner similar to temperature or humidity-based alarm messages. The handling of such alarms will vary from system to system, the details of which are omitted herein. In general, each system will provide active and ongoing notification of an alarm condition until the alarm condition is manually acknowledged by an operator.

Thus, the above described embodiment provides additional alarm capabilities not found in the prior art. In particular, the above-described embodiment generates a new type of alarm related to a composite measure of environmental quality. This type of alarm can alert a system operator to a combination of conditions in a room or space that contribute to a poor overall quality regardless of whether a particular condition is out of normal bounds. Poor environmental quality can lead to reduced productivity and/or reduced health of the people working in the building, both of which are undesirable. The IEQ-related alarm allows such conditions to be detected early, and does not delay notice of poor conditions until one of the individual parameters advances to an alarm-inducing level.

Another advantage of the above-described embodiment is the availability of granular and/or room level IEQ information that may be used by the control station 318 (or other nodes) for monitoring, verification, and/or control of the indoor environmental quality on a building-wide or system-wide basis. The control station 318 may also use the IEQ information for trending and to isolate developing problems in one or more areas of the building.

Figure 5:
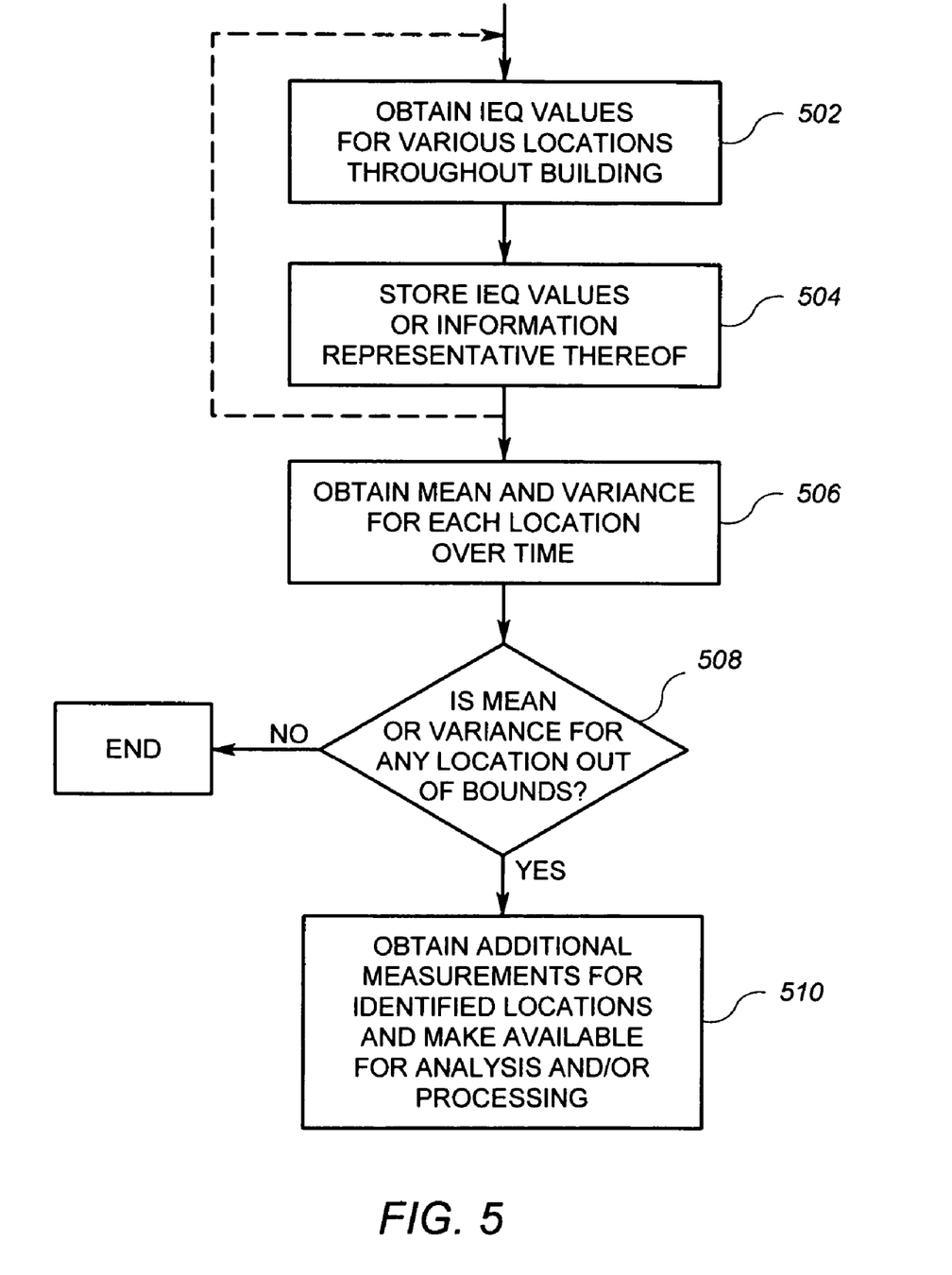
FIG. 5 shows a flow diagram of an exemplary set of operations that may be performed by a control station using data obtained by the arrangement of FIG. 4.

FIG. 5 shows one exemplary embodiment of an operation that may be performed by the control station 318 or some other computing device based on the available IEQ values from each of the Microsystems (or from each of the rooms of the building 300). The operations of FIG. 5 may be used to log IEQ values and to analyze statistically the IEQ values to identify problem areas. The operations of FIG. 5 use the IEQ values to determine whether further data from localized areas is necessary for troubleshooting. The operations of FIG. 5 will be discussed as being performed by the control station 318, and particularly by the data processor 318a thereof.

In step 502, the control station 318 obtains IEQ values pertaining to each room or space in the building 300, or at least in a large portion thereof. The IEQ values pertaining to each room may suitably be the IEQ values for each individual microsystem in a room or space, or a composite or derivative IEQ value for the room based on the IEQ values of all of the Microsystems in the room. In either event, the control station 318 receives the IEQ values for each room from the corresponding field controller for the room. By way of example, as discussed above, the control station 318 receives the IEQ values from the rooms 304.1 and 304.2 from the field controller 412. (See FIG. 4). In a similar manner, the control station 318 receives the IEQ values from the hall space portion 304.4 from the field controller 416.

Thereafter in step 504, the control station 318 stores the IEQ values for each room/space in a storage device, which may be suitable storage devices or memory within the control station 318 itself, not shown, but which would be known to those of ordinary skill in the art. The ongoing storage of IEQ values allows the IEQ values to be available for other applications, as well as the application described below. Steps 502 and 504 may suitably repeat in a periodic manner without regard to when steps 506, 508 and 510 are executed.

In step 506, the control station 318 determines a mean and variance for the IEQ values of each space, location or room over a defined period of time. The control station uses the values stored in step 504 as well as previously stored IEQ values to generate the mean and variance of the IEQ values. The mean and variance is determined for each location (room, space or microsystem location) over the defined period of time. In general, the mean defines the overall IEQ for the location over a period of time, which may be a few hours or a few days. The variance determines how much the IEQ value has varied from its mean, indicating the volatility of conditions in the room (or adjacent the microsystem).

In step 508, the control station 318 determines, for each room or microsystem, whether the overall (mean) IEQ value is unusually high (or low), and whether the IEQ value variance is unusually high. For example, the control station 318 may compare the mean IEQ value for each location with a mean IEQ value calculated of all (or at least a large number) of locations, and may further compare the variance for each location with a mean of all variances in a large number of locations.

If an abnormal mean or variance for a location is detected, then, in step 510, the control station 318 logs all the variables for the corresponding location over a period of time. Thus, if a problem in the overall IEQ of space 304.1 is detected in step 508, then the control station 318 in step 510 obtains the individual temperature, humidity, CO2, CO, TVOC, flow and other constituent values of room 304.1 to attempt to isolate the source of the problem.

In addition, in step 510, the variables for any identified problem areas are subjected to analysis, such as determining the mean and variance over time, in order to identify potential issues within the room. The results of such analysis may be made available to a user via the user interface 318b of the control station 318, or made available remotely via an Internet connection.

A technician is therefore provided both with notice that a particular area may be experiencing an environmental quality issue, and with additional data for each individual condition. Such information may be used to isolate problems that lead to poor environmental quality that may be addressed through proper remediation.

The above described operations is one example of how the granular IEQ values for the building 300 may be used to improve environmental quality. Other examples identified by those of ordinary skill in the art may readily benefit from the IEQ value acquisition and storage elements of the embodiments described above.

It is noted that some embodiments may not require a field controller. For example, in an alternative embodiment, the microsystems 406.x, 408.x and 410.x 302 may communicate with the control station via a wireless network. As discussed above, each of the Microsystems 406.x, 408.x and 410.x includes wireless communication capability. Because the network of microsystems 406.x, 408.x and 410.x extends throughout the building 300, a path may be drawn between any microsystem 406.x, 408.x and 410.x to the data processor 318 through a daisy chain connection of Microsystems such that no single microsystem requires a long range RF communication capability.

It will appreciated that the above described embodiments are exemplary, and that those of ordinary skill in the art may readily devise their own implementations and modifications that incorporate the principles of the invention and fall within the spirit and scope thereof.

I claim:

1. An arrangement, comprising:
    a plurality of wireless microsystems, each microsystem operable to measure a plurality of indoor environmental quality-related parameters and operable to communicate first information pertaining to the measured parameters wirelessly to a network device,
    a data processor operably coupled to receive the first information from the network device, and further configured to generate a metric value of an indoor environmental quality of at least a first space based at least in part on the first information, the metric value dependent upon each of the measured parameters of at least a first of the plurality of microsystems, and
    a controller operable to generate control information based on the metric value and communicate the control information to at least one actuator,
    wherein the metric value of the indoor air quality is based in part on information representative of at least one HVAC-related measurement and information representative of at least one of a total volatile organic compound measurement, a $CO_2$ measurement, a CO measurement, a light measurement and a sound measurement.

2. The arrangement of claim 1, wherein the at least one HVAC-related measurement includes at least one selected from the group consisting of a temperature measurement, a humidity measurement, and a flow measurement.

3. The arrangement of claim 2, wherein the measurement of the concentration of one or more gas substances includes at least one selected from the group consisting of a $CO_2$ concentration measurement, a noxious gas concentration measurement, and a CO concentration measurement.

4. The arrangement of claim 1, wherein the plurality of indoor environmental quality-related parameters includes HVAC-related measurements and gas concentration measurements.

5. The arrangement of claim 1, wherein the first information comprises a first indoor environmental quality value based on at least one HVAC-related measurement and at least one gas concentration measurement, and wherein the metric value is based on a plurality of first indoor environmental quality values from the plurality of microsystems.

6. The arrangement of claim 1, wherein the network device comprises a microsystem operable to perform measurements and communicate information wirelessly to the data processor.

7. The arrangement of claim 1, wherein the network device is operable to communicate information to the data processor via at least one intermediate device, and wherein the network device is operable to communicate information wirelessly to the intermediate device.

8. The arrangement of claim 1, wherein the network device forms part of a field controller device, and wherein the data processor forms part of the field controller device.

9. The arrangement of claim 1, wherein the network device forms part of a field controller device, and wherein the data processor forms part of a control station remote from the field controller device.

10. The arrangement of claim 1, wherein each microsystem is operable to update and communicate the first information on an ongoing basis, and wherein the data processor is further configured to update the metric value of the indoor environmental quality on an ongoing basis.

11. The arrangement of claim 1 wherein the controller comprises the data processor.

12. An arrangement, comprising:
a plurality of wireless microsystems, each microsystem operable to measure a plurality of indoor environmental quality-related parameters and operable to communicate first information pertaining to the measured parameters wirelessly to a network device, at least one measured parameter including an HVAC-related parameter and at least one other parameter selected from a group consisting of a total volatile organic compound measurement, a $CO_2$ measurement, a CO measurement, a light measurement and a sound measurement,
a data processor operably coupled to receive the first information from the network device, and further configured to generate a metric value of an indoor environmental quality of at least a first space based at least in part on the first information, the metric value dependent upon each of the measured parameters of at least one of the plurality of microsystems, and
a controller operable to generate control information based on the metric value and communicate the control information to at least one actuator.

13. The arrangement of claim 12, wherein the central data processor is further operable to generate a metric value in the form of a statistic using a plurality of an indoor environmental quality (IEQ) index values, each IEQ index value having a value dependent upon each of the measured parameters of at least a first microsystem.

14. The arrangement of claim 13, wherein each microsystem is operable to generate an IEQ index value and provide the IEQ index in the first information.

15. The arrangement of claim 13, wherein the IEQ index value is dependent upon at least two measured parameters selected from a group consisting of a total volatile organic compound measurement, a $CO_2$ measurement, a CO measurement, a light measurement and a sound measurement.

16. The arrangement of claim 13, wherein the data processor is further operable to:
compare the metric value to a first threshold limit; and
generate a first alarm message based on whether the metric value exceeds the first threshold limit.

17. The arrangement of claim 16, wherein:
the data processor is further operable to generate alarm messages if at least one individual measured parameter exceeds a corresponding alarm threshold; and
the data processor is further is operable to generate the first alarm message based on whether the metric value exceeds the first threshold limit and each of the at least one individual measured parameters is less than the corresponding alarm threshold.

18. The arrangement of claim 17, wherein the data processor is further operable to generate a metric value in the form of a statistic using a plurality of an indoor environmental quality (IEQ) index values, each IEQ index value having a value dependent upon each of the measured parameters of at least a first microsystem.

19. The arrangement of claim 12, wherein the network device comprises a microsystem operable to perform measurements and communicate information wirelessly to the central data processor.

20. The arrangement of claim 12, wherein the network device forms part of a field controller device, and the data processor forms a part of the field controller device.

21. The arrangement of claim 12, wherein each microsystem is operable to update and communicate the first information on an ongoing basis, and wherein the central data processor is further configured to update the metric value of the indoor environmental quality on an ongoing basis.

22. The arrangement of claim 12, wherein the controller comprises the data processor.

* * * * *